US00PP22542P3

(12) United States Plant Patent

Shaw et al.

(10) Patent No.: US PP22,542 P3

(45) Date of Patent: Mar. 6, 2012

(54) STRAWBERRY PLANT NAMED 'BENICIA'

(50) Latin Name: ***Fragaria×ananassa* Duch.**
Varietal Denomination: Benicia

(75) Inventors: Douglas V. Shaw, Davis, CA (US); Kirk D. Larson, Santa Ana, CA (US)

(73) Assignee: The Regents of the University of California, Oakland, CA (US)

( * ) Notice: Subject to any disclaimer, the term of this patent is extended or adjusted under 35 U.S.C. 154(b) by 269 days.

(21) Appl. No.: 12/657,923

(22) Filed: Jan. 29, 2010

(65) Prior Publication Data

US 2011/0191920 P1 Aug. 4, 2011

(51) Int. Cl.
*A01H 5/00* (2006.01)

(52) U.S. Cl. ..... Plt./208

(58) Field of Classification Search ..... Plt./208
See application file for complete search history.

(56) References Cited

U.S. PATENT DOCUMENTS

| | | | | | |
|---|---|---|---|---|---|
| PP4,538 | P | * | 5/1980 | Bringhurst et al. | Plt./209 |
| PP5,262 | P | * | 7/1984 | Voth et al. | Plt./208 |
| PP8,708 | P | * | 5/1994 | Voth et al. | Plt./209 |
| PP13,469 | P3 | * | 1/2003 | Larson et al. | Plt./208 |
| PP19,472 | P3 | * | 11/2008 | Shaw et al. | Plt./208 |

OTHER PUBLICATIONS

UPOV ROM GTITM Computer Database, GTI Jouve Retrieval Software 2011/10 Citation for 'Benecia'.*

Anonymous. "Benecia Strawberry Plants & Mojave Strawberry Plants" Strawberry Plants.org Jun. 2, 2010 available at http://strawberryplants.org/2010/06/benicia-strawberry-plants-mojave-starberry-plants/.*

* cited by examiner

*Primary Examiner* — Wendy C Haas

(74) *Attorney, Agent, or Firm* — Kilpatrick Townsend & Stockton LLP

(57) ABSTRACT

'Benicia' is a short-day (June bearing) type cultivar that produces fruit over an extended period when treated appropriately in arid, sub-tropical climates. When treated with appropriate planting regimes, 'Benicia' has larger fruit and produces individual-plant yields greater than that of 'Camarosa' (U.S. Plant Pat. No. 8,708). It further produces similar quantities of fruit per plant but develops larger and higher quality fruit than 'Ventana' (U.S. Plant Pat. No. 13,469.

4 Drawing Sheets

Genus and species: The strawberry cultivar of this invention is botanically identified as *Fragaria×ananassa* Duch.

Variety denomination:

The variety denomination is 'Benicia'.

BACKGROUND OF THE INVENTION

This invention relates to a new and distinctive short-day type cultivar designated as 'Benicia'. The new cultivar was the result of a cross performed in 2004 between the cultivar 'Palomar' (U.S. Plant Pat. No. 19,472) and unreleased germplasm accession Cal 0.18-601 (unpatented). Accession Cal 0.18-601 was chosen as a parent due to its large, firm, and high quality fruit and medium plant vigor. 'Benicia' was first fruited at an experimental orchard near Winters, Calif. in 2005, where it was selected, originally designated Cal 4.39-1, and propagated asexually by runners. Following selection and during testing, the plant of this selection was designated 'C225'. It was later designated 'Benicia' for introduction into commerce. Asexual propagules from this original source have been tested in Watsonville, Calif., in Irvine, Calif., and to a limited extent in grower fields starting in 2007. The cultivar is stable and reproduces true to type in successive generations of asexual reproduction.

BRIEF SUMMARY OF THE INVENTION

'Benicia' is a short-day (June bearing) type cultivar that produces fruit over an extended period when treated appropriately in arid, sub-tropical climates. When treated with appropriate planting regimes, 'Benicia' has larger fruit and produces individual-plant yields greater than that of 'Camarosa' (U.S. Plant Pat. No. 8,708). It further produces similar quantities of fruit per plant but develops larger and higher quality fruit than 'Ventana'(U.S. Plant Pat. No. 13,469).

BRIEF DESCRIPTION OF THE DRAWINGS

The figures depict various characteristics of the 'Benicia' cultivar.

DETAILED DESCRIPTION OF THE INVENTION

Figure 1:
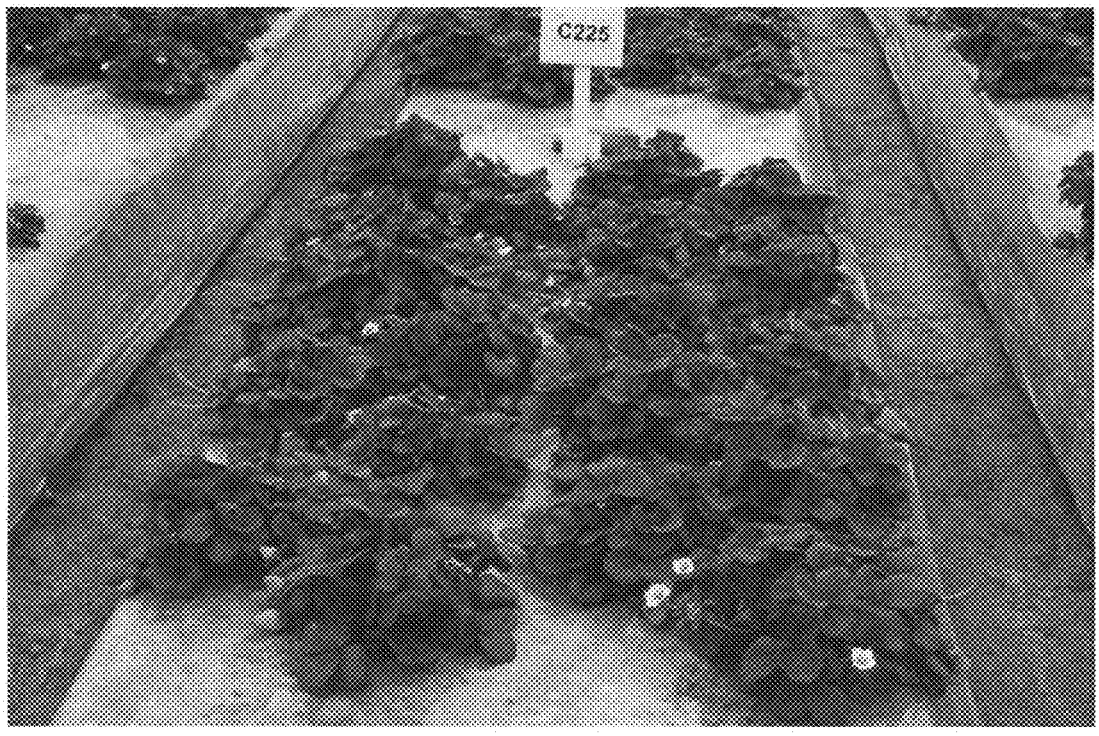
FIG. 1 shows the general flowering and fruiting characteristics of the plant in a field planting.
Figure 2:
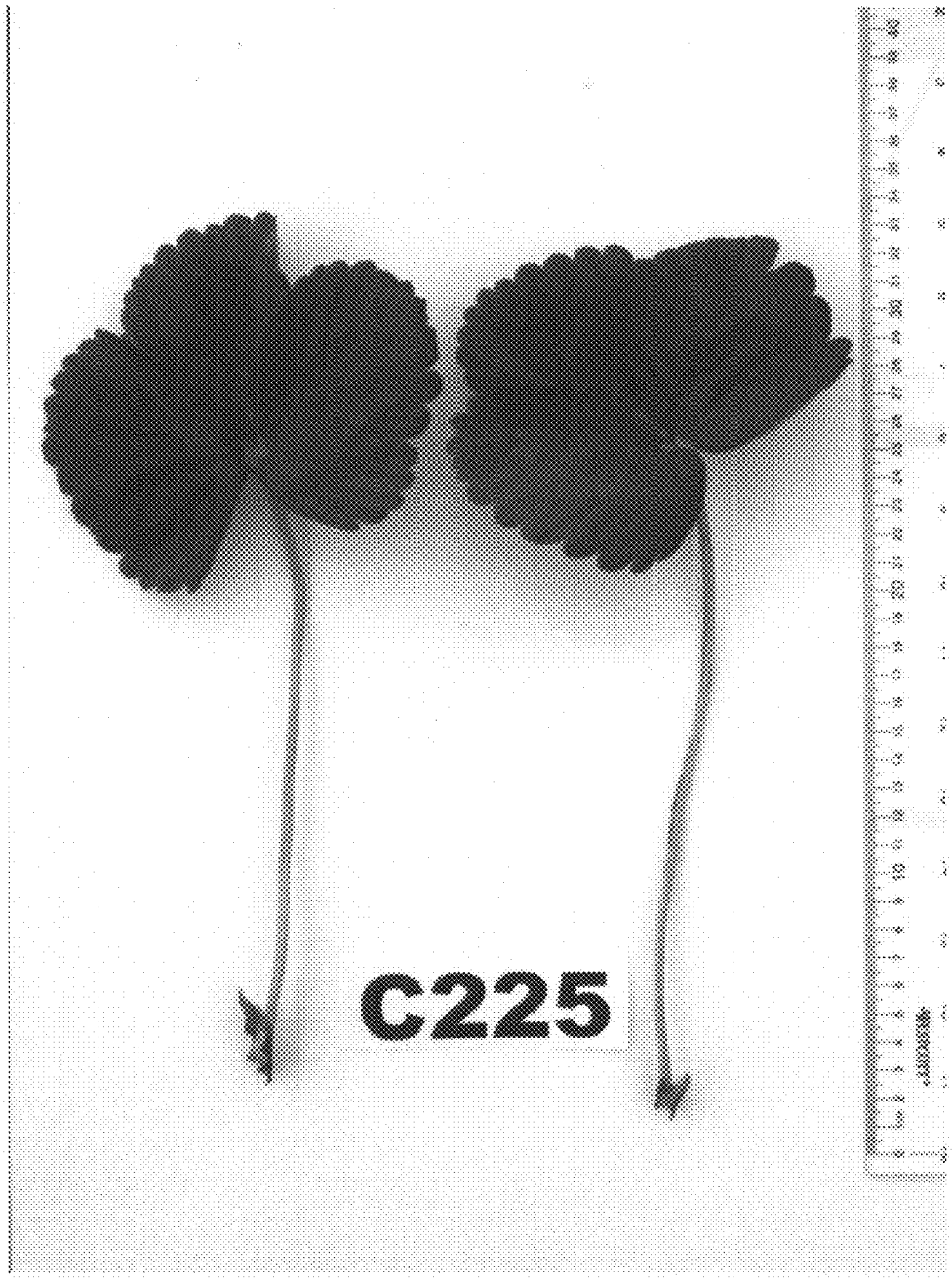
FIG. 2 shows a typical leaf at mid-season.
Figure 3:
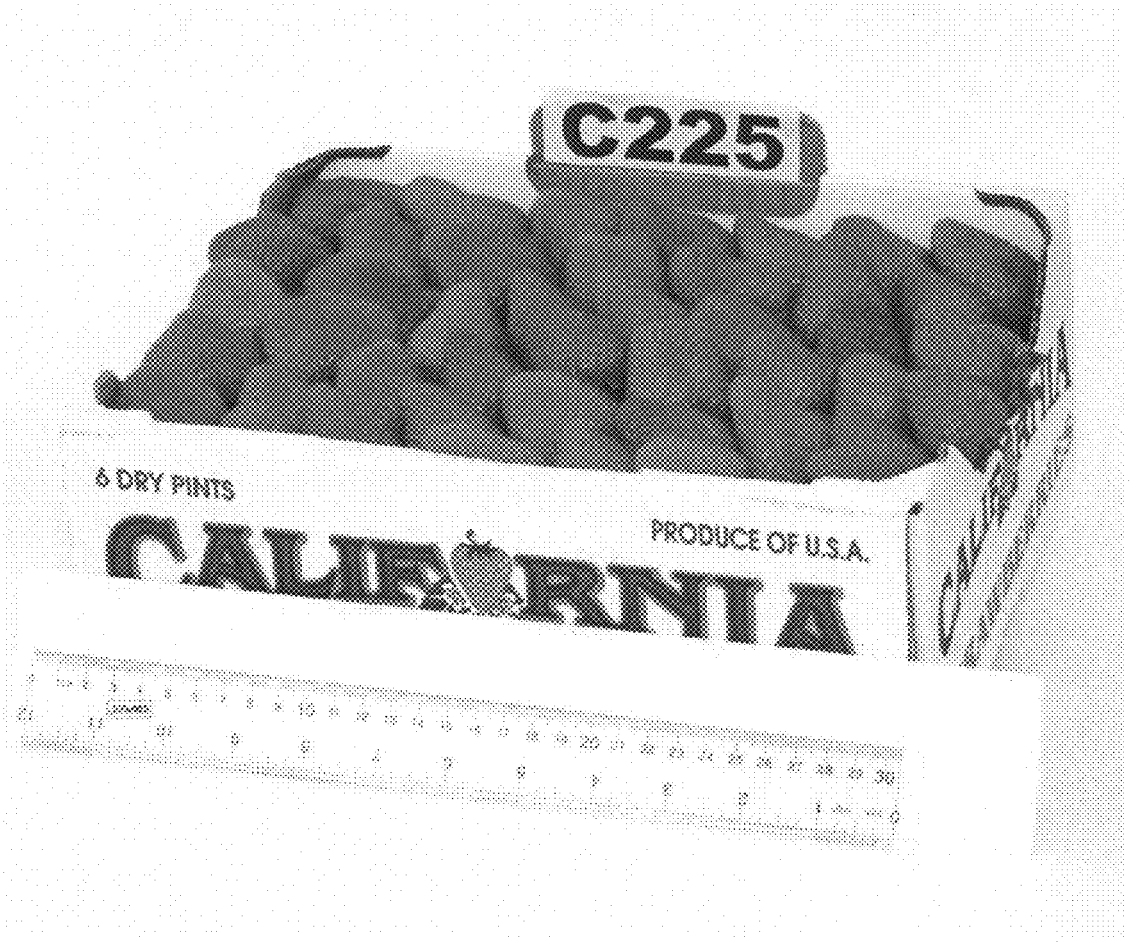
FIG. 3 shows representative mid-season fruit.
Figure 4:
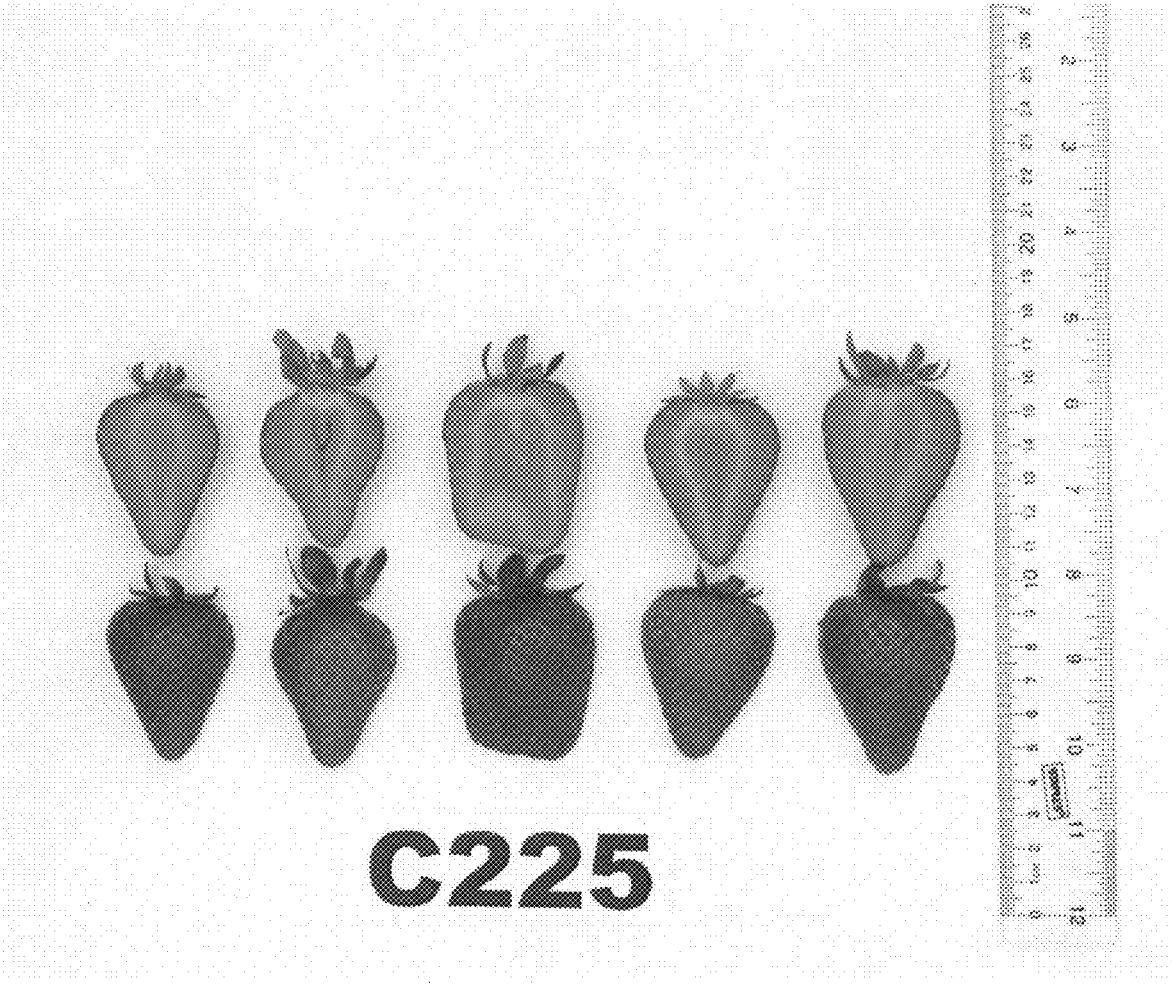
FIG. 4 shows a cross-section of representative mid-season fruit.

'Benicia' is typical of short-day strawberry cultivars and produces fruit over an extended period when treated appropriately in arid, subtropical climates. The production pattern for 'Benicia' is similar to that of 'Camarosa' and 'Palomar', although it is somewhat earlier to initiate fruiting with most cultural treatments. 'Benicia' initiates fruiting somewhat later than 'Ventana' when established in very early fall, but has a production pattern similar to 'Ventana' with most cultural treatments. 'Benicia' will be of special interest for winter plantings, where 'Camarosa', 'Ventana', and 'Palomar' have been successful, and in summer plantings where 'Pajaro' (U.S. Plant Pat. No. 4,538) and 'Chandler' (U.S. Plant Pat. No. 5,262) have been successful. Color references have been made to the Munsell Color Chart.

Plants and foliage:

Fruiting plants of 'Benicia' are similar in morphology to 'Ventana', although slightly more open and erect, and somewhat smaller throughout most of the production season with most cultural treatments. 'Benicia' plants are larger than those of 'Palomar' and similar in size to 'Camarosa' in most production environments. Comparative statistics for foliar characteristics near mid-season are given for 'Benicia' and three comparison cultivars in Table 1. Individual leaflets for 'Benicia' are smaller and less rounded than for 'Camarosa'. Further, the leaflets are similar in shape but smaller than those of 'Ventana' or 'Palomar'. Leaves (including petioles) for 'Benicia' are similar in length to 'Ventana' and 'Camarosa', but shorter than 'Palomar' mostly due to shorter petiole length. Petioles for 'Benicia' are generally longer and thinner than those of the comparison cultivars. The adaxial (upper) and abaxial (lower) surfaces of leaves for 'Benicia' are similar in color to 'Camarosa' and darker than 'Ventana' leaves at mid season. Leaves of 'Benicia' have consistently more concavity than 'Camarosa', less concavity than 'Palomar' and are similar to those for 'Ventana'. Serrations at mid season are more pointed than 'Camarosa', but similar in shape and number to 'Ventana' and 'Palomar'.

TABLE 1

Foliar and plant characteristics for 'Benicia', 'Camarosa', 'Palomar', and 'Ventana'.

| | Cultivar | | | |
|---|---|---|---|---|
| Foliar Character | 'Camarosa' | 'Ventana' | 'Palomar' | 'Benicia' |
| Plant height (mm) | | | | |
| mean | 299 | 277 | 262 | 304 |
| range | 280-320 | 250-300 | 250-290 | 280-370 |
| Plant spread (mm) | | | | |
| mean | 431 | 432 | 388 | 438 |
| range | 395-490 | 370-485 | 360-455 | 390-500 |
| Mid-tier leaflet | | | | |
| Length (mm) | | | | |
| mean | 100 | 92 | 88 | 98 |
| range | 93-105 | 55-110 | 76-93 | 90-120 |
| Width (mm) | | | | |
| mean | 87 | 79 | 72 | 82 |
| range | 80-100 | 73-90 | 65-80 | 70-90 |
| Mid-tier leaf | | | | |
| Length (mm) | | | | |
| mean | 290 | 314 | 244 | 318 |
| range | 267-325 | 235-350 | 160-282 | 290-330 |
| Width (mm) | | | | |
| mean | 178 | 169 | 156 | 167 |
| range | 152-210 | 150-190 | 128-175 | 150-187 |
| Leaf components | | | | |
| Petiole length (mm) | | | | |
| mean | 194 | 220 | 169 | 224 |
| range | 170-220 | 190-240 | 150-175 | 210-230 |
| Petiole diameter (mm) | | | | |
| mean | 5.1 | 4.9 | 4.5 | 4.2 |
| range | 4-6 | 4-6 | 4-5 | 3-5 |
| Petiolule length (mm) | | | | |
| mean | 8.5 | 6.1 | 5.5 | 7.0 |
| range | 6-10 | 5-7 | 4-6 | 5-8 |
| # leaflets/leaf | 3 | 3 | 3, rarely 4 or 5 | 3 |
| Leaf convexity | Some convex, most flat to slight concave | flat to very concave | concave to very concave | |
| Serrations | | | | |
| number/leaf | 19.5 | 20.6 | 20.6 | 18.9 |
| range | 18-21 | 18-23 | 18-23 | 17-20 |
| shape | rounded, some semi-pointed | semi-pointed | semi-pointed | semi-pointed |
| Leaf pubescence | light-moderate | light-moderate | moderate-light | moderate |
| Petiole pubescence | | | | |
| density | heavy | moderate-heavy | heavy | moderate-heavy |

TABLE 1-continued

Foliar and plant characteristics for 'Benicia', 'Camarosa', 'Palomar', and 'Ventana'.

| Foliar Character | Cultivar | | | |
|---|---|---|---|---|
| | 'Camarosa' | 'Ventana' | 'Palomar' | 'Benicia' |
| direction | perpendicular | perpendicular to acropetal | perpendicular | perpendicular |
| Petiole color (Munsell) | 2.5 GY 8/9 | 2.5 GY 8/9 | 2.5 GY 8/9 | 2.5 GY 9/8 |
| Stipule length (mm) | | | | |
| mean | 33.8 | 31.9 | 33.3 | 31.5 |
| range | 30-45 | 25-40 | 25-41 | 20-41 |
| Stipule color | | | | |
| core | 7.5 GY 9/4 | 2.5 GY 9/8 | 10 Y 9/9 | 5 GY 8/8 |
| margins | 7.5 GY 8/7 | 10 Y 8/11 | 2.5 GY 9/8 | 7.5 GY 9/4 |
| Stolon base diameter (mm) | 1.7 | 1.5 | 2.3 | 1.9 |
| Stolons per nursery mother plant | 28.0 | 18.8 | 25.5 | 28.2 |
| Venation | | | | |
| pattern | pinnate | pinnate | pinnate | pinnate |
| color | 10 GY 7/8 | 5 GY 8/8 | 2.5 GY 8/9 | 7.5 GY 9/4 |

Disease and pest reaction:

'Benicia' is moderately resistant to powdery mildew (*Sphaerotheca macularis*), but is moderately susceptible to Anthracnose crown rot (*Colletotrichum acutatum*), and very susceptible to *Verticillium* wilt (*Verticillium dahliae*). It is moderately susceptible to *Phytophthora* crown rot (*Phytophthora cactorum*) and common leaf spot (*Ramularia tulasnei*) (Table 2). When treated properly, it has tolerance to two-spotted spider mites (*Tetranychus urticae*) equal to that of the comparison cultivars. 'Benicia' is tolerant to strawberry viruses encountered in California.

TABLE 2

Disease resistance scores for 'Benicia' and three comparison cultivars.

| Genotype | *Phytophthora* Resistance Score (5 = best) | *Verticillium* Resistance Score (5 = best) | *Colletotrichum* Resistance Score (5 = best) |
|---|---|---|---|
| 'Camarosa' | 3.06 | 3.08 | 3.1 |
| 'Ventana' | 2.06 | 2.89 | 2.7 |
| 'Palomar' | 2.81 | 4.14 | 3.0 |
| 'Benicia' | 3.50 | 2.08 | 2.6 |

*Phytophthora* and *Verticillium* scores were obtained in evaluations conducted between 2008-2009;
*Colletotrichum* was evaluated in 2009.

Flowering, fruiting, fruit, and production characteristics:

'Benicia' is similar to other California short-day strawberry cultivars (e. g. 'Ventana', 'Camarosa', and 'Palomar') in that it will flower over an extended period and into spring or summer, given appropriate local temperature and horticultural conditions. With very early plantation establishment (before October 1 in California), 'Benicia' produces fruit slightly later than 'Ventana' and 'Palomar' but earlier than 'Camarosa'. With later plantation establishment, 'Benicia' initiates fruit as early as 'Ventana' and 'Palomar', with earlier production timing than 'Camarosa'. Comparative statistics for flower and fruit characteristics near mid-season are given for the four cultivars in Table 4. The primary flowers for 'Benicia' are similar in size to 'Ventana', with a calyx that is distinctly larger than the corolla on primary fruit. The sepals are similar in length and shape to 'Camarosa' and 'Ventana'. The calyx for 'Benicia' varies in position but frequently has a slight neck early in the season. Each primary flower has 6-8 petals, slightly more than the comparison cultivars on average. The fruit shape for 'Benicia' can vary, but is typically medium to long conic, which can be flattened or slightly obovate. It is easily distinguished by fruit shape from 'Camarosa' (shortened and flattened conic), or 'Ventana' (medium symmetrical conic), and 'Palomar' (short symmetrical conic). External and internal fruit color for 'Benicia' is similar to that of 'Camarosa' and darker than that of 'Ventana' or 'Palomar' (Table 3). Achenes vary from yellow to dark red, and are even with the fruit surface or slightly indented.

'Benicia' has been tested under a variety of cultural regimes, and optimal performance is obtained when nursery treatments and nutritional programs similar to those of 'Camarosa', 'Ventana', and 'Palomar' are used. In general, plants of 'Benicia' are less vigorous than 'Camarosa' or 'Ventana' with very early season planting, but more vigorous than 'Palomar'. 'Benicia' retains excellent fruit quality in summer planting systems.

When treated with appropriate planting regimes, 'Benicia' has larger fruit and produces individual-plant yields greater than that of 'Camarosa'. It produces similar quantities of fruit per plant but develops larger and higher quality fruit than 'Ventana' (Table 5). Commercial appearance ratings have been equal to or better than those for all of the comparison cultivars, especially 'Camarosa'. Fruit from 'Benicia' is substantially firmer than fruit from 'Ventana', but similar in firmness to the other comparison cultivars. Subjectively, 'Benicia' has outstanding flavor. The fruit will be exceptional for both fresh market and processing, and will be useful for home gardening purposes.

TABLE 3

Foliar and fruit color characteristics for 'Benicia' and three comparison cultivars.

| Color | Cultivar | | | |
|---|---|---|---|---|
| Character | 'Camarosa' | 'Ventana' | 'Palomar' | 'Benicia' |
| Leaf color (CIELAB) Adaxial L* | | | | |
| mean | 37.1 | 40.0 | 35.2 | 38.2 |
| range | 34.8-41.3 | 33.2-39.2 | 33.7-37.0 | 35.0-41.9 |

TABLE 3-continued

Foliar and fruit color characteristics for 'Benicia' and three comparison cultivars.

| Color Character | Cultivar 'Camarosa' | 'Ventana' | 'Palomar' | 'Benicia' |
|---|---|---|---|---|
| a* | | | | |
| mean | −13.1 | −10.8 | −8.9 | −13.1 |
| range | −11.5--16.8 | −9.1--13.3 | −7.0--11.9 | −7.3--17.3 |
| b* | | | | |
| mean | 16.6 | 15.5 | 11.3 | 17.4 |
| range | 15.3-17.7 | 12.8-19.5 | 9.1-12.3 | 9.6-23.9 |
| Munsell | 5 GY 5/6 | 2.5 GY 4/3 | 5 GY 4/3 | 2.5 GY 4/3 |
| Abaxial | | | | |
| L* | | | | |
| mean | 51.5 | 48.5 | 49.0 | 51.2 |
| range | 48.8-53.4 | 45.6-50.2 | 36.3-50.6 | 47.9-54.5 |
| a* | | | | |
| mean | −14.7 | −12.3 | −12.2 | −13.6 |
| range | −13.7--16.5 | −11.3--13.3 | −11.2--13.3 | −11.4--15.9 |
| b* | | | | |
| mean | 22.3 | 20.7 | 18.6 | 20.5 |
| range | 19.6-26.2 | 17.6-22.7 | 14.7-22.2 | 17.5-24.5 |
| Munsell | 7.5 GY 8/7 | 7.5 GY 8/7 | 7.5 GY 9/4 | 2.5 GY 8/6 |
| Fruit color (CIELAB) | | | | |
| External | | | | |
| L* | | | | |
| mean | 36.5 | 34.4 | 33.7 | 33.2 |
| range | 33.2-40.0 | 31.7-36.3 | 28.9-36.5 | 31.1-38.6 |

TABLE 3-continued

Foliar and fruit color characteristics for 'Benicia' and three comparison cultivars.

| Color Character | Cultivar 'Camarosa' | 'Ventana' | 'Palomar' | 'Benicia' |
|---|---|---|---|---|
| a* | | | | |
| mean | 33.3 | 33.6 | 34.4 | 33.3 |
| range | 28.6-39.3 | 25.9-38.7 | 24.3-39.7 | 31.5-36.6 |
| b* | | | | |
| mean | 17.9 | 15.8 | 15.4 | 14.6 |
| range | 10.9-26.2 | 10.4-20.9 | 11.5-23.6 | 10.2-20.2 |
| Munsell | 7.5 R 4/11 | 7.5 R 5/13 | 5 R 3/7 | 2.5 R 7/10 |
| Internal | | | | |
| L* | | | | |
| mean | 53.7 | 52.4 | 48.4 | 49.5 |
| range | 44.2-60.9 | 48.6-57.8 | 42.1-54.9 | 42.0-58.5 |
| a* | | | | |
| mean | 29.6 | 28.8 | 24.7 | 29.8 |
| range | 24.8-33.8 | 23.9-33.9 | 21.1-29.0 | 20.9-34.9 |
| b* | | | | |
| mean | 26.3 | 23.7 | 20.2 | 23.9 |
| range | 21.4-30.1 | 18.1-27.5 | 18.2-23.8 | 19.2-26.7 |
| Munsell | 7.5 R 5/13 | 5 R 5/13 | 7.5 R 6/12 | 7.5 R 5/13 |
| Achene color | | | | |
| Munsell | 2.5 Y 7/10 | 10 Y 8/11 | 7.5 R 8/12 | 5 R 3/7 |

TABLE 4

Flower and fruit characteristics for 'Benicia' and three comparison cultivars.

| Character | Cultivar 'Camarosa' | 'Ventana' | 'Palomar' | 'Benicia' |
|---|---|---|---|---|
| Petal number | | | | |
| mean | 5.7 | 6.2 | 5.7 | 6.6 |
| range | 5-8 | 5-8 | 5-6 | 6-8 |
| Petal shape | | | | |
| apex | truncate to slightly obtuse | truncate to slightly obtuse | truncate to slightly obtuse | truncate to slightly obtuse |
| base margin | attenuate entire | attenuate entire | attenuate entire | attenuate entire |
| Petal length (mm) | | | | |
| mean | 14.2 | 15.1 | 18.3 | 15.5 |
| range | 13-16 | 14-17 | 15-21 | 15-17 |
| Petal width (mm) | | | | |
| mean | 14.8 | 16.9 | 18.2 | 16.7 |
| range | 13-16 | 16-19 | 15-22 | 15-18 |
| Flower position (relative to foliage) | most even some exposed | even to exposed | even to exposed | even to exposed |
| Calyx diam. (mm) | | | | |
| mean | 48.1 | 45.2 | 57.5 | 49.6 |
| range | 40-52 | 42-52 | 51-61 | 45-53 |
| Corolla diam. (mm) | | | | |
| mean | 37.4 | 39.7 | 44.4 | 39.6 |
| range | 32-44 | 38-42 | 42-47 | 39-41 |
| Sepal length (mm) | | | | |
| mean | 20.6 | 19.7 | 23.5 | 20.1 |
| range | 16-25 | 19-22 | 19-28 | 19-21 |

TABLE 4-continued

Flower and fruit characteristics for 'Benicia' and three comparison cultivars.

| Character | Cultivar | | | |
|---|---|---|---|---|
| | 'Camarosa' | 'Ventana' | 'Palomar' | 'Benicia' |
| Sepal width (mm) | | | | |
| mean | 11.5 | 9.8 | 11.7 | 11.5 |
| range | 10-13 | 8-11 | 10-13 | 11-12 |
| Sepal color (Munsell) | 7.5 GY 5/7 | 2.5 GY 8/9 | 7.5 GY 7/9 | 7.5 GY 7/9 |
| Pedicel length (mm) | | | | |
| mean | 229 | 259 | 183 | 238 |
| range | 220-240 | 230-290 | 150-210 | 210-290 |
| Pedicel diameter (mm) | | | | |
| mean | 3.1 | 4.3 | 3.7 | 4.2 |
| range | 2-4 | 3-5 | 3-5 | 3-5 |
| Pedicel color | 2.5 GY 6/8 | 2.5 GY 9/8 | 5 GY 8/8 | 2.5 GY 9/8 |
| Fruit shape | | | | |
| Fruit length (mm) | | | | |
| mean | 48.7 | 50.5 | 49.9 | 52.0 |
| range | 43-53 | 45-60 | 43-55 | 50-58 |
| Fruit width (mm) | | | | |
| mean | 40.7 | 45.2 | 44.4 | 43.4 |
| range | 37-51 | 41-53 | 38-55 | 42-48 |
| Length/ width | | | | |
| ratio | 1.21 | 1.12 | 1.13 | 1.20 |
| range | 1.0-1.4 | 1.0-1.2 | 1.0-1.3 | 1.0-1.4 |
| subjective | Obovate-flat | Medium conic | Short conic | Medium-long conic |
| Primary/secondary fruit comparison | | | | |
| size (subjective) | 40-60% | 50-60% | 50-60% | 50-60% |
| shape | similar shape, more conic | similar shape | similar shape | similar shape |
| Extent/size of hollow core | small-absent | Small | small-absent | small-absent |
| Calyx | | | | |
| position | indented-neck | even-reflexed | even-indented | even-indented |
| size relative to fruit | equal or less than fruit diameter | equal or less than fruit diameter | equal or greater than fruit diameter | equal or greater than fruit diameter |
| Seed position | indented-extruded | even-extruded | even-indented | even-indented |
| Adherence of Calyx to Fruit | Weak | Intermediate | Weak | Weak |

Flower and plant measurements obtained on Apr. 3, 2008; fruit measurements obtained between May 10-20, 2008.

TABLE 5

Performance of 'Benicia' and three comparison cultivars evaluated in Watsonville, CA between 2008-9.

| Item | Yield (g/plant) | Appearance Score (5 = best) | Fruit Size (g/fruit) | Firmness |
|---|---|---|---|---|
| 'Camarosa' | 2,137 | 2.7 | 28.6 | 10.1 |
| 'Ventana' | 2,616 | 3.0 | 33.3 | 9.8 |

TABLE 5-continued

Performance of 'Benicia' and three comparison cultivars evaluated in Watsonville, CA between 2008-9.

| Item | Yield (g/plant) | Appearance Score (5 = best) | Fruit Size (g/fruit) | Firmness |
|---|---|---|---|---|
| 'Palomar' | 2,667 | 3.7 | 34.1 | 10.4 |
| 'Benicia' | 2,566 | 3.6 | 33.7 | 10.0 |

All plants for these trials were harvested from a commercial nursery near Macdoel, CA between October 15-16, and transplanted after 6-7 days to supplemental storage. Fruit harvest was initiated in early April and continued through the last week of August. (52" 2-row beds, 17,300 plants/acre).

What is claimed is:

1. A new and distinct cultivar of strawberry plant having the characteristics substantially as described and illustrated herein.

* * * * *